United States Patent
Babkin et al.

(10) Patent No.: US 8,475,441 B2
(45) Date of Patent: Jul. 2, 2013

(54) ISOTHERM-BASED TISSUE ABLATION CONTROL SYSTEM

(75) Inventors: Alexei Babkin, Albuquerque, NM (US); Peter Littrup, Bloomfield Hills, MI (US)

(73) Assignee: CryoMedix, LLC, San Diego, CA (US)

( * ) Notice: Subject to any disclaimer, the term of this patent is extended or adjusted under 35 U.S.C. 154(b) by 704 days.

(21) Appl. No.: 12/643,919

(22) Filed: Dec. 21, 2009

(65) Prior Publication Data

US 2010/0168725 A1 Jul. 1, 2010

Related U.S. Application Data (60) Provisional application No. 61/203,313, filed on Dec. 23, 2008.

(51) Int. Cl.
*A61B 18/02* (2006.01)

(52) U.S. Cl.
USPC .................. 606/21; 606/22; 607/105

(58) Field of Classification Search
USPC .................. 606/20–26; 607/104, 105
See application file for complete search history.

(56) References Cited

U.S. PATENT DOCUMENTS

| | | |
|---|---|---|
| 4,602,628 A | 7/1986 | Allen, Jr. |
| 4,946,460 A | 8/1990 | Merry et al. |
| 5,207,674 A | 5/1993 | Hamilton |
| 5,305,825 A | 4/1994 | Roehrich et al. |
| 5,334,181 A | 8/1994 | Rubinsky et al. |
| 5,520,682 A | 5/1996 | Baust et al. |
| 5,531,742 A * | 7/1996 | Barken ................ 606/21 |
| 5,573,532 A | 11/1996 | Chang et al. |
| 5,674,218 A | 10/1997 | Rubinsky et al. |
| 5,733,247 A | 3/1998 | Fallon |
| 5,787,715 A | 8/1998 | Dobak, III et al. |
| 5,946,290 A | 8/1999 | Mizutani et al. |
| 5,956,958 A | 9/1999 | Dobak, III et al. |

(Continued)

FOREIGN PATENT DOCUMENTS

| | | |
|---|---|---|
| AU | 2004201679 | 5/2004 |
| CA | 2440777 | 9/2009 |

(Continued)

OTHER PUBLICATIONS

PCT International Search Report and Written Opinion of the International Searching Authority, issued May 4, 2010, Application No. PCT/US2009/069046.

(Continued)

*Primary Examiner* — Linda Dvorak
*Assistant Examiner* — Jocelyn D Ram
(74) *Attorney, Agent, or Firm* — Convergent Law Group LLP; Rick Batt (57) ABSTRACT

A system and method for use with at least one cryoprobe for the treatment of biological tissue controls the energy applied to the tissue. The invention receives live procedure data such as temperature information from locations along the pathway of the cryogenic liquids, and calculates a procedure signature or profile based on the procedure data. In one embodiment, volumetric isotherms are calculated. The procedure signature is compared to a planning signature based on previously acquired image data and estimates of the thermal gradients from models. The system and method are further configured to automatically regulate the application of power based on analysis of the planning data to the procedure data.

18 Claims, 4 Drawing Sheets

U.S. PATENT DOCUMENTS

| | | | |
|---|---|---|---|
| 5,978,697 A | 11/1999 | Maytal et al. | |
| 6,074,572 A | 6/2000 | Li et al. | |
| 6,237,355 B1 | 5/2001 | Li | |
| 6,355,029 B1 | 3/2002 | Joye et al. | |
| 6,471,694 B1 | 10/2002 | Kudaravalli et al. | |
| 6,485,422 B1 * | 11/2002 | Mikus et al. | 600/439 |
| 6,530,234 B1 | 3/2003 | Dobak, III et al. | |
| 6,530,946 B1 | 3/2003 | Noda et al. | |
| 6,537,271 B1 | 3/2003 | Murray et al. | |
| 6,551,309 B1 | 4/2003 | LePivert | |
| 6,679,081 B2 | 1/2004 | Marsala | |
| 6,685,720 B1 | 2/2004 | Wu et al. | |
| 6,726,653 B2 | 4/2004 | Noda et al. | |
| 6,773,408 B1 | 8/2004 | Acker et al. | |
| 6,893,433 B2 | 5/2005 | Lentz | |
| 6,893,653 B2 | 5/2005 | Abraham et al. | |
| 6,904,305 B2 | 6/2005 | Tsekos | |
| 6,972,015 B2 | 12/2005 | Joye et al. | |
| 6,981,382 B2 | 1/2006 | Lentz et al. | |
| 6,984,233 B2 | 1/2006 | Hooven | |
| 7,004,936 B2 | 2/2006 | Ryba et al. | |
| 7,022,120 B2 | 4/2006 | Lafontaine | |
| 7,081,111 B2 | 7/2006 | Svaasand et al. | |
| 7,192,426 B2 | 3/2007 | Baust et al. | |
| 7,220,252 B2 | 5/2007 | Shah | |
| 2002/0083717 A1 | 7/2002 | Mullens et al. | |
| 2004/0215294 A1 | 10/2004 | Littrup et al. | |
| 2005/0203505 A1 | 9/2005 | Megerman et al. | |
| 2005/0261753 A1 | 11/2005 | Littrup et al. | |
| 2006/0155268 A1 * | 7/2006 | Amir et al. | 606/21 |
| 2007/0031338 A1 | 2/2007 | Zabinski | |
| 2007/0112251 A1 | 5/2007 | Nakhuda | |
| 2007/0119190 A1 | 5/2007 | Yan | |
| 2007/0277550 A1 | 12/2007 | Li et al. | |
| 2008/0027420 A1 * | 1/2008 | Wang et al. | 606/21 |
| 2008/0033419 A1 * | 2/2008 | Nields et al. | 606/27 |
| 2008/0119834 A1 | 5/2008 | Vancelette et al. | |
| 2008/0119839 A1 | 5/2008 | Vancelette | |
| 2008/0121759 A1 | 5/2008 | Behrens et al. | |
| 2008/0125764 A1 | 5/2008 | Vancelette et al. | |
| 2008/0161784 A1 | 7/2008 | Hogan et al. | |
| 2009/0270851 A1 | 10/2009 | Babkin | |
| 2009/0318804 A1 * | 12/2009 | Avital et al. | 600/439 |
| 2010/0305439 A1 * | 12/2010 | Shai et al. | 600/439 |
| 2011/0251607 A1 * | 10/2011 | Kruecker et al. | 606/34 |

FOREIGN PATENT DOCUMENTS

| | | |
|---|---|---|
| GB | 2432875 A | 6/2007 |
| WO | 92/04872 | 4/1992 |
| WO | 00/09054 | 2/2000 |
| WO | 2004/064914 | 8/2004 |
| WO | 2004086936 A2 | 10/2004 |
| WO | 2005/063136 | 7/2005 |
| WO | 2005081731 A2 | 9/2005 |
| WO | 2007044980 A2 | 4/2007 |
| WO | 2009/067497 | 5/2009 |
| WO | 2009/131978 | 10/2009 |

OTHER PUBLICATIONS

Patent Abstracts of Japan; JP2003-075004; Cryogenic Apparatus; Atsutoshi Ishikawa; Publication Date: Dec. 3, 2003.

Patent Abstracts of Japan; JP2004-275732; Refrigeration Source for Cryoablation Catheter; Ryba et al.; Publication Date: Jul. 10, 2004.

* cited by examiner

ISOTHERM-BASED TISSUE ABLATION CONTROL SYSTEM

CROSS-REFERENCE TO RELATED APPLICATIONS

The present application claims the benefit of provisional patent application No. 61/203,313, filed Dec. 23, 2008, the entirety of which is incorporated by reference.

BACKGROUND OF THE INVENTION

The present invention relates to planning, monitoring and regulation of temperature gradients, or isotherms, for thermal treatment of tissue, and in particular, the cryoablation of tissue.

Thermal treatment of tissues has become an increasingly effective method of treatment for a variety of pathological cases. For example, malignancies in body organs such as liver, lungs, kidney, prostate, breast, and other organs are successfully treated by thermal ablation when heat or cold irreversibly destroys pathological tissue. Target temperatures are generally emphasized since irreversible changes that destroy a cell occur more reliably at those levels, but the time that those target temperatures are maintained are also important.

For example, consistent cell death using heat usually requires temperatures greater than 50° C. for over one (1) minute, while tissue freezing usually requires two (2) cycles of target tissue temperatures less than −20° C. for greater than three (3) minutes each, interspaced by a passive thaw of greater than three (3) minutes. These general assumptions are variable depending upon local tissue conditions of: 1) adjacent blood vessels, or vasculature, acting as heat sinks; 2) tissue perfusion from blood flow of the micro vasculature, and; 3) the overall thermal characteristics of the tissue, such as thermal conductivity and capacity, which appear related to the ratio of fluid and/or fibrous content.

In connection with cryo-treatments, the localized anatomy surrounding a target area to be treated (e.g., frozen), or tumor, may be assessed by various imaging techniques such as ultrasound (US), X-ray, computed tomography (CT) or magnetic resonance imaging (MRI).

Ultrasound clearly shows only the bright echoes from the leading edge of the ice closest to the ultrasound probe. The interface between frozen and non-frozen tissue has marked sound speed differences. Nearly all echoes are reflected with minimal signal penetrating the iceball. This causes marked shadowing behind the leading ice edge, obscuring all posterior structures.

Plain X-ray technique is only capable of showing the border of the lower density frozen tissue. This is possible, however, only if the tissue is sufficiently compressed to allow detection of the density difference as a projected shadow that is perpendicular to the main axis of the x-ray. Both ultrasound and x-ray techniques thus provide only partial information concerning the size and position of three-dimensional frozen tissue, and cannot define the full three-dimensional cryoablation volume contained within the frozen tissue.

CT and MRI techniques are preferred over ultrasound and x-ray since they can produce a reconstructed tissue volume from the usual sequence of axial images. In addition, they can be performed before, during and after intravenous contrast enhancement to assess the vascularity of the target tumor relative to the surrounding tissues. CT is more readily available than interventional MR units within the community and doesn't have metal incompatibility issues. However, MRI can provide greater contrast between the different soft and/or frozen tissues than CT and has temperature-sensitive imaging sequences. Unlike CT, MRI uses no ionizing radiation, but uses a powerful magnetic field and pulsed radiofrequency fields to cause the hydrogen nuclei to produce a rotating magnetic field detectable by the scanner. These signals can be manipulated by additional magnetic fields to build up enough information to construct a volumetric image of the target object.

U.S. Pat. Nos. 6,773,408 and 6,904,305 relate to MRI medical interventional procedures and therapies, applying ablation energy to the target tissues, and further relate to monitoring such therapy by magnetic resonance application. The technology described in the '408 and '305 patents are partially based on the fact that certain known MRI sequences are temperature sensitive, so that magnetic resonance data acquired using these procedures will indicate changes in the temperature of the tissues. For example, a magnetic resonance parameter referred to as T1 (spin-lattice relaxation time) will vary with temperature. If a magnetic resonance imaging apparatus is actuated to acquire T1 for various volume elements within the subject, the data for different elements will vary with temperature, at least within a tissue having generally the same composition. The data can be displayed as a visible image, and hence different temperatures can be shown by the differences in brightness or color within the displayed image. Unfortunately, this approach can only display the degree of the heating within a location within the body being heated.

These procedures have been well known but have not been widely adopted in the medical practice. Magnetic resonance imaging instruments include large, precise magnets which are arranged to impose a high magnetic field but also severely limit access to the target subject. Moreover, the MRI instruments must be such so as to be substantially unaffected by the MRI system's powerful magnetic field. Medical instruments constructed of non-MRI-compatible materials may be subjected to powerful undesired forces generated by magnetic interaction between the instrument and the MRI magnetic field that may distort the MRI image. Additionally, electrical circuits used within the MRI environment must be shielded because they may be subject to induced currents generated within the electrical circuitry. Induced current can lead to uncontrolled processes such as distortion of data or control signals. Electric currents induced by an external magnetic field interacting with components of electronic circuitry could have a distorting effects during its normal operation. For example, electronic circuits with switching components which are switching at high frequencies (e.g., computers) and with potential for emission of electromagnetic fields must be strictly shielded.

Another shortcoming of MRI is that commercially available MRI systems do not detect and display temperatures within frozen tissue. Research has been done evaluating ultrashort echo-times to assess the R2* parameter and generate temperature assessment within the iceball but these sequences are complex and specialized to limited centers.

What is needed is a system that provides capability of direct identification or localization of the isotherms within frozen tissue with reliable identification of the external border of the ablation volume. What is further needed is a system that is capable of providing accurate estimation of the size and position of an ablation volume in cryosurgery, since it is a goal to ablate all pathological tissue while damaging as little as possible of healthy tissue surrounding the pathological tissue. What is further needed is to enable a physician, during a procedure, to have accurate information of what tissues have been frozen. What is further needed is a system adapted to render the border of the ablation volume, or alternatively a system facilitating accurate estimation of the size and position of such a border, to decrease danger of surgical complications and avoid various deleterious consequences to the long-term health and quality of life of the recovering patient.

Attempts to provide systems for MRI-guided cryosurgery are described in U.S. Pat. No. 5,978,697 and US Pat. Application No. 2006/0155268. The '697 patent describes a system with inner and outer modules for MRI-guided cryosurgery comprising an MRI magnet having an opening for enabling access of a surgeon to the patient who is accommodated inside the MRI room, a line member of a surgical device extending through MRI magnet channel, a surgical device itself including: (a) an operating member for operating the patient; (b) a control member for controlling the operating member, the control member being positioned externally to the MRI room; (c) a line member having a first end connectable to the operating member and a second end connectable to said control member, wherein a portion of the line member is received within the channel of the MRI magnet. The line member includes an underground portion extending through an underground channel. The operating member is a cryogenic probe including a Joule-Thomson heat exchanger, and the line member is a gas tube. The control member includes a microprocessor for controlling the operation of cryosurgical device. A display member is positioned within the MRI room, the display member being electrically connected to the microprocessor for providing information relating to the operation. The cryogenic probe includes a thermal sensor electrically connected to the microprocessor.

A disadvantage of the system described in the '697 patent is the separation of control functions into inner and outer modules that requires two operators of the surgical equipment, a first operator being a surgeon positioned within the inner module, i.e., within magnetic field of the MRI equipment, and a second operator whose function includes inputting gas control commands and reporting to the surgeon the cryosurgery system status which the surgeon from his position into inner module cannot see and estimate for-himself, and cannot directly control. Another disadvantage of the system described in the '697 patent is an impossibility to display and control temperatures within ablated frozen tissue because the thermal sensor placed at the distal end of the cryoprobe can provide only information about temperature in the central point of ablation volume.

Application No. 2006/0155268 describes an MRI-guided and compatible cryosurgery system that comprises a cryoprobe operable to be cooled by expansion of high-pressure cooling gas though a Joule-Thomson orifice. This schematically presented system enable a surgeon positioned next to a patient and within an MRI magnetic environment both to monitor progress of an intervention by observing MR images of the intervention in real time, and to fully control aspects of operation of a cryosurgery. The apparatus described may remotely control a fluid supply source positioned external to the magnetic environment thereby enabling real-time MRI-guided control of a cryoablation process. A schematically presented embodiment enables calculation and display of borders of an ablation volume surrounding a cooled cryoprobe, and further enables automated control of elements of a cryoablation procedure, which elements are triggered when shape and position of the calculated ablation volume are found. The schematic intervention module may comprise a plurality of cryoprobes, an MRI-compatible template operable to guide insertion of the cryoprobe into the body of the patient, and a thermal sensor operable to be positioned at a selected position within the body. The cryoprobe may comprise a thermal sensor operable to report temperatures within the cryoprobe or to report temperature external to the cryo probe.

A shortcoming of Application No. 2006/0155268 is that complete information about temperature distribution within the frozen volume of ablation with thermal sensors is unavailable. Additionally, the described temperature distribution profile across a schematic frozen tissue formed by the tip of cryosurgical probe, to the external surface of the frozen volume, appears somewhat arbitrary and unrealistic.

Thus, there is a need to have a thermal ablation system that can provide to a physician isotherm distribution within the target tissue in order to plan, monitor and control tissue ablation using thermal response for anatomic and tissue characterization.

SUMMARY OF THE INVENTION

A system for use with at least one cryoprobe for the treatment of biological tissue with thermal ablation includes receiving procedure data wherein the procedure data comprises an inflow temperature at a location along an inflow conduit of the probe, and an outflow temperature at a location along the outflow conduit. The processor calculates a procedure signature or profile based on the procedure data and compares the procedure signature to a planning signature based on previously acquired image data and or model of the tissue.

In another embodiment the planning signature is a planning isotherm volume of tissue and the procedure signature is a tissue isotherm volume obtained during the intervention, or cryoablation. In another embodiment the processor is further operative to compare the information and automatically regulate the flowrate of a cryogen to the cryoprobe.

In another embodiment, a method is described for treatment of a target volume of biological tissue using at least one thermal tissue ablation apparatus. The method comprises a number of steps: 1) receiving procedure data, the procedure data comprising an inlet temperature of the fluid within the inlet conduit and at a location within the tissue treatment portion of the apparatus and an outlet temperature of the fluid within the outlet conduit and at a location within the tissue treatment portion of the apparatus; 2) determining a procedure signature based on the procedure data; and 3) comparing the procedure signature to a previously determined planning signature. In another aspect of the invention, the method further comprises automatically applying an amount of thermal energy to the tissue based on the comparing step. In another aspect of the invention, the method further comprises the step of providing the thermal ablation apparatus wherein the fluid is a cold liquid with a freezing point less than $-90°$ C. another aspect of the invention, the cold liquid is one liquid selected from the group of propane, perfluropropane, R-124, and R-1270. In another aspect of the invention, the comparing step is performed substantially continuously during the treatment and the amount of thermal energy being applied is adjusted based on real time information determined by the comparing step. In one embodiment, a computer includes a feedback loop and calculates the difference between the two signatures and determines the amount of adjustment to the power parameters of the cryoprobe to force the procedure signature to match or converge with the planned signature.

According to one aspect of the invention a method of treatment planning comprises observing a marker, or seed, that is deposited prior to treatment within the target volume and well-visualized by US, CT or MRI. The well-visualized marker is used at the beginning of the treatment session to confirm location of tumor margins and vascularity in relation to actual probe placement. The marker is then used to validate anatomic location of tumor margins and vascularity in relation to developing treatment margins during treatment, thus serving as one of the inputs to continuously adjusted probe power during treatment protocol.

According to a further aspect of the invention there is provided a method which allows monitoring of tissue response to thermal changes induced by probes inserted into the target treatment region, whereby that tissue thermal response is reflected in the difference between the inlet temperature of substance entering the exchange chamber at the probe tip and the outlet temperature as it exits the chamber.

The disclosure and invention specifically include combination of features of various embodiments as well as combinations of the various embodiments where possible. The description, objects and advantages of the present invention will become apparent from the detailed description to follow, together with the accompanying drawings.

BRIEF DESCRIPTION OF THE DRAWINGS

FIG. 2b is a schematic view showing an isotherm distribution for the tumor shown in FIG. 2a.

FIG. 3b is schematic view showing an isotherm distribution for the tumor shown in FIG. 3a.

DETAILED DESCRIPTION OF THE INVENTION

Figure 1A:
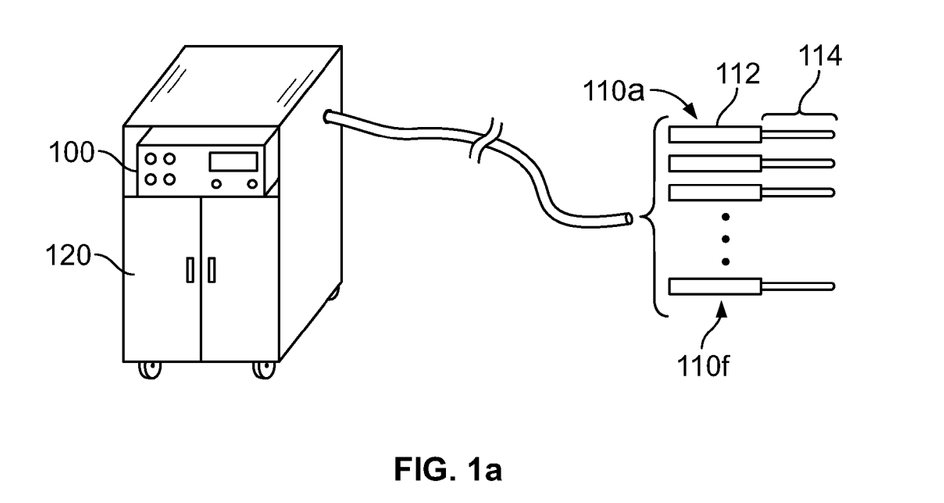
FIG. 1a is an illustration of a tissue ablation control system in accordance with one embodiment of the present invention.

FIG. 1a illustrates a thermal ablation control system in accordance with one embodiment of the invention. Computer 100 is shown in communication with one or more cryoprobes 110 a-f. Computer 100 may be a general purpose computer including a processor. Computer is also in communication with (or has incorporated therein) a controller (not shown) to power the cryoprobes. In the case of a cryoprobe, the controller may control such parameters as flowrate of a cryogen liquid to the cryoprobe, temperature of the cryogen, actuate valves, etc. Additionally, a cryogen tank, refrigerator, pump, electrical supply, and other equipment may be housed in cabinet 120.

The probe 110a includes a handle 112 and a tissue treatment portion 114 or freeze zone. The tissue treatment portion is shown as a rigid shaft having a pointed tip. However, the shaft may be flexible and atraumatic in other embodiments. Additionally, although this embodiment is directed to a cryoprobe, other probes are contemplated and intended to be within the scope of the invention except where excluded by the scope of the appended claims. In use, the shaft 114 is inserted into the target tissue. This may be performed in, for example, percutaneous or open procedures.

The tissue treatment portion encloses an exchange chamber fed by a fluid inlet conduit. The shape of the exchange chamber may vary widely and in one embodiment, comprises an elongate cavity. A fluid outlet conduit is fluidly joined to the exchange chamber to return the fluid to the fluid source or reservoir tank (not shown). The tissue treatment portion applies energy to the tissue, and in the case of a cryo-treatment, freezes the tissue in the vicinity of the tissue treatment portion. An example of a cryoprobe and system that can provide a cryotherapy is described in U.S. Publication No. 20090270851 to Babkin et al., the entirety of which is incorporated by reference.

In another embodiment the cryoprobe does not have an exchange chamber per se. The conduit follows a path leading to and from the tissue treatment portion. More than one conduit may be provided and the conduit's cross section may vary in shape and size.

As mentioned above, the present invention includes use of temperature data from the probe. To this end, probes that are useful with the system of the present invention include a sensor within each the fluid inlet conduit and fluid outlet conduit. Preferably, the sensors, such as thermocouples, are located in the tissue treatment portion or freeze zone of the probe and in some cases, in the most distal portion of the tip. The sensors may also be placed at the immediate entry and exit to the exchange chamber, or anywhere within the insulated distal portion of the probe. In this manner, a live or real time temperature difference at the cryoprobes 110a-f may be obtained and sent to computer 100 during a pre-treatment or treatment procedure.

Figure 1B:
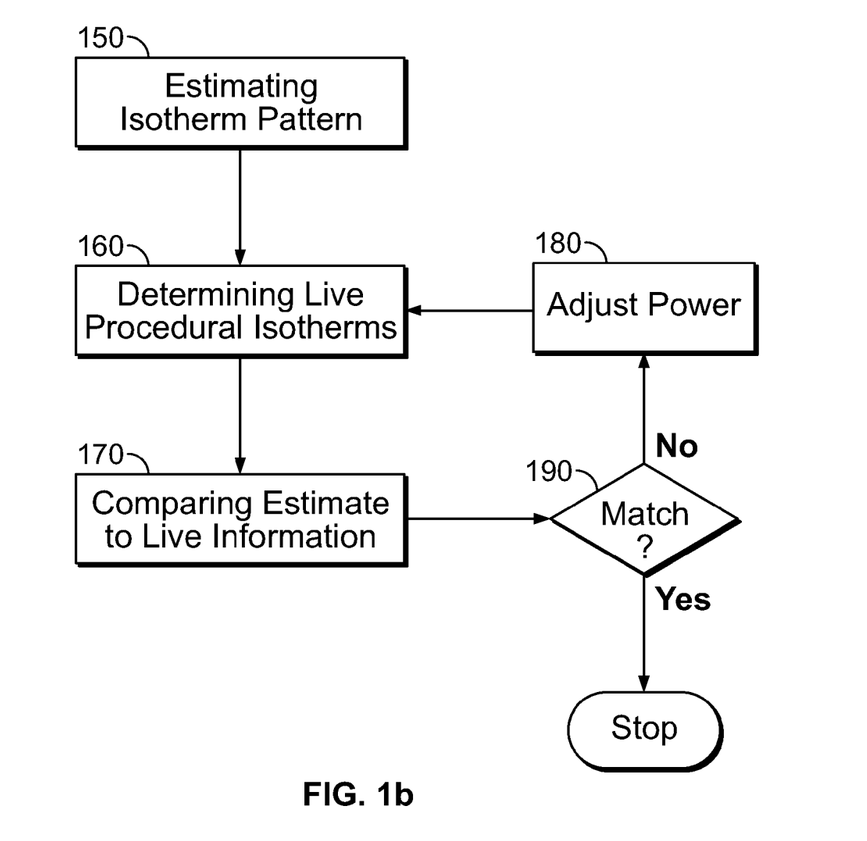
FIG. 1b is a flow chart showing the steps of a method in accordance with one embodiment of the present invention.

FIG. 1b illustrates the general steps of one embodiment of the present invention. The steps shown in FIG. 1b include: (a) estimating a treatment signature based on various information including, for example, a planned isotherm distribution 150; (b) determining a procedural signature or isotherm distribution based on receiving procedure data including, for example, a real-time temperature gradient between fluid inflow and outflow of a tissue treatment portion of the ablation apparatus 160; and (c) comparing the procedure signature to the planned treatment signature 170. In one embodiment, the energy or power supplied to the tissue is adjusted automatically based on the above described comparing step as depicted by reference numeral 180. Once the procedural profile matches the estimated profile, the treatment may be stopped as depicted in step 190 of FIG. 1b.

The estimated or planned treatment profile or signature may have a wide variety of forms. In one embodiment of the invention, the treatment signature is a planned isotherm distribution for a target volume of tissue. Determining a thermal response to the target tissue however depends on a number of variables not the least of which is vascularity or tissue perfusion. Thermal responses of tissue relate in part to physiological changes caused by tumor perfusion. These changes are probably superceded by major heat-sink effects of adjacent vasculature during ablation. Several current investigations suggest significantly higher tumor recurrence rates for radiofrequency (RF) or other heat-based ablation when the tumor has a margin abutting a major blood vessels having greater than 3 mm in diameter. Blood flow is distinctly different between arteries and veins but a general rule in cryotherapy holds that the heat-sink effect of veins greater than 6 mm in diameter will prevent luminal freezing that occludes vessel flow, assuming the power levels of current Joule-Thomsontype (JT) cryoprobes (Endocare, Inc, Irvine, Calif.). However, most ablation procedures are done without contrast which limits both tumor margin differentiation and clear identification of adjacent vessels.

The heat sinks, whether arising from vascularity or otherwise, may be incorporated into the tissue model or simulation to determine the planned isotherm distribution for the target tissue. A tissue modeling can account for major determinants of tissue response to heating and freezing. Modeling estimates for cryotherapy have been developed for prostate treatment planning, but their use of a urethral warmer serves also as an excellent surrogate for the heat-sink effects of a major blood vessel. Similar to RF ablation simulations, these models use the classic bioheat equation: $C^*(\partial T/\partial t)=\Delta(k\Delta T)+w_b C_b(T_b-T)+q_{met}$, where $C^*$ is the volumetric specific heat of the tissue, T the temperature, t time, k the thermal conductivity of the tissue, $w_b$ the blood perfusion volumetric flow rate per unit volume of tissue, $C_b$ the volumetric specific heat of the blood, $T_b$ the blood temperature entering the thermally treated area, and $q_{met}$ is the metabolic heat generation. The models also stress the non-linearity of changes in thermal conductivity and specific heat as phase changes occur during freezing, as well as the great uncertainty of temperature dependency on blood perfusion and adjacent vasculature. However, none of currently existing computer modeling efforts take into account the variations in actual location of final probe placements during the procedure, much less the resultant differences in flow parameters experienced by each probe because of these placement inaccuracies.

Computer simulations have thus not become part of standard cryotherapy since they not represent actual freeze conditions due to placement inaccuracies. Final locations of the cryoprobes within the target tissue can only be monitored in real time by the physician using available ultrasound and/or CT imaging, or additional thermocouple data for prostate cryotherapy. No reliable imaging parameters have been described to assess correlates of thermal conductivity or heat capacity related to tissue components, such as greater water or collagen content (i.e., fibrous consistency). Therefore, the effects of adjacent vasculature can only be estimated for probe placement considerations, relating to overall total cryoprobe number and spacing.

Figure 2A:
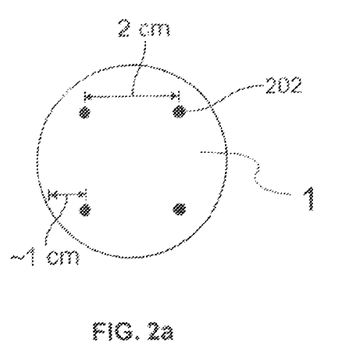
FIG. 2a is a schematic view showing a plurality of cryoprobes distributed within a tumor without adjacent vascularity.
Figure 2B:
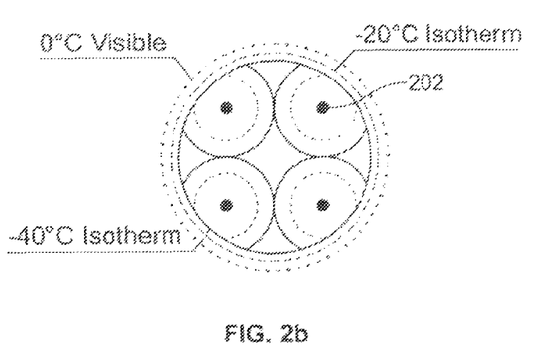

FIG. 2a demonstrates a model for estimating the probe requirements to cover a larger tumor 1 (i.e., >3 cm diameter) with Joules Thompson probes 202 of 2.4 mm shaft diameter. This follows a current estimate of the "1-2 rule", whereby cryoprobes 202 are placed in a circumferential manner no more than 1 cm from the tumor margin and less than 2 cm apart from each other within the tumor 1. Assuming a relatively non-fibrous tumor without adjacent vascularity and applying the above described equation for isotherms, an isotherm distribution is shown in FIG. 2b where the −40° C. isotherm generally covers only the contour of the tumor, and the −20° C. and 0° C. isotherms extend up to 5 and 10 mm from the tumor margin, respectively. As shown, the visible ice observed by CT/US/MRI is predicted to closely match the 0° C. isotherm up 10 mm beyond the underlying tumor margin.

Figure 3A:
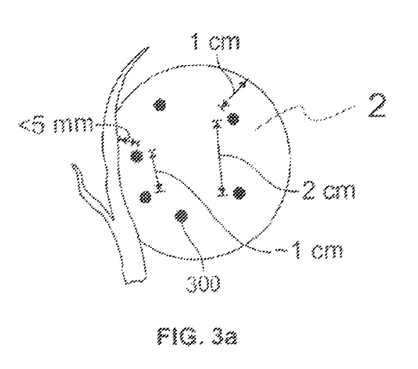
FIG. 3a is a schematic view showing a plurality of cryoprobes distributed within a tumor with adjacent vascularity.
Figure 3B:
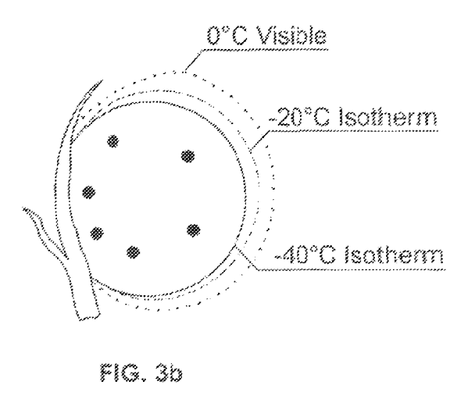

The effects of major blood vessels (i.e., >3 mm diameter) adjacent to the tumor 2 are illustrated in FIG. 3a and FIG.3b, including the estimated required alteration in probe placement 300 to still achieve cytotoxic isotherms throughout the tumor. The heat sink of the vessel is overcome by placing the cryoprobes closer together (i.e., ~1 cm) and even closer to the adjacent vessel (<5 mm) as shown in FIG. 3a. This produces a sharp transition line of <2 mm from the vessel lumen temperature of ~30° C. to the lethal isotherms within the tumor as shown in FIG. 3b.

Predictive modeling of cryotherapy is more accurate when tumor size and adjacent vessel location and size are known. However, the overall freezing response, let alone tissue consistency, is difficult to predict without interstitial thermocouple feedback. These are currently placed around the periphery of a prostate gland during cryotherapy to assure lethal temperatures extending to the margin of this organ. The anterior margin of the prostate also has numerous abutting vessels of Santorini's plexus of veins. However, other organs are not as easily accessed as the prostate (e.g., liver, kidney, retroperitoneum) or have greater puncture risk (e.g., lung), such that thermocouples are avoided in favor of accurate cryoprobe placements and visual assessment of ice formation (i.e., 0° C. isotherm) by either CT/US/MRI. Yet, clear visualization of ice margins in relation to underlying tumor margins is frequently sub-optimal. Artifacts from the cryoprobes degrade both CT and US images which are the most commonly used and available guidance modalities. The tumor margins or adjacent vessels cannot be well seen without IV contrast during probe placement so that a greater chance exists for both inadequate treatment of all tumor margins by cytotoxic temperatures as well as for potential greater complications. The present invention discloses new concepts to improve localization of the target tissue in combination with new cryotechnology for more accurate and automated control of cytotoxic isotherms.

In some embodiments of the present invention, a marker such as a visible clip, implant, or seed, is placed within target masses prior to ablation for better treatment planning and localization. A radio-opaque clip placed before a cryotherapy procedure helps localize the tumor in relation to its margins and adjacent vessels. If a metallic clip had been placed prior to an ablation session, a simple contrast injection done immediately prior to cryoprobe placements could verify tumor margins and adjacent vessels in relation to 3D clip localization within the tumor target. Even after the contrast bolus has passed, the tumor margins and adjacent vessels can still be localized in a volumetric imaging sequence (e.g., CT/MRI) according to the location of the clip which is highly visible. The clip now serves as the static 3D reference point for remainder of the treatment session. The developing margins of iceball can then be viewed in relation to the anatomic location of the clip for 3D feedback in order to immediately plan cryoprobe distribution and interactively adjust treatment powers of all cryoprobes.

The next aspect of the present invention relates to improved ablation control by characterization of the tissue response for one or more probes. The following describes a system and methodology whereby the tissue response surrounding a probe can be categorized by the instantaneous temperature differences ΔT between ingoing and outgoing substances to the probe tip. While the present invention may also include an embodiment that produces heat at the probe tip from hot flowing substances going into the probe, this embodiment includes cold flowing substances, or cryogens, that flow into and out of a chamber at the probe tip. The rate of heat transfer to the cryogen reflects the rate of freezing within the surrounding tissues. Though a number of cryogens may be used, it is desirable in a preferred embodiment that the cryogen has a sufficient thermal conductivity and capacity to provide accurate rapid or instantaneous feedback of changing temperatures of the surrounding tissue. The speed and accuracy of monitoring the tissue freezing response is proportional to the thermal conductivity and capacity of the circulating cryogen. Additionally, in this embodiment, the contact surface of the probe is made of a highly conductive material.

The apparatus for applying energy to the tissue comprises a distal tissue treatment portion, a fluid inlet conduit, a fluid outlet conduit, and an exchange chamber in fluid communication with the inlet conduit and outlet conduit. A fluid enters the exchange chamber via the fluid inlet and exits the exchange chamber via the fluid outlet. The exchange chamber is disposed within the tissue treatment portion of the apparatus.

In one embodiment, the apparatus is a cryoprobe in contact with target tissue without adjacent vasculature and consequently, the probe would be diagnostic as a relatively low heat sink, and the temperature of flowing cryogen would change by a small amount. This change would be detected by temperature sensors such as thermocouples monitoring the temperature of the cryogen passing through the exchange chamber within the inlet and outlet tubes within the tissue treatment portion or the "freeze zone" of the apparatus. In one embodiment, the apparatus is a probe and the freeze zone comprises the probe tip. However, in other embodiments, the freeze zone comprises additional sections of the catheter that transfer energy to the surrounding tissue. Conversely, a high heat sink tissue location, such as a probe lying close to a blood vessel, would show a large change in temperature of the cryogen passing through the heat exchange chamber.

In this manner direct knowledge of the continuous heat sink effects of the local tissue surrounding a cryoprobe could be monitored. The freezing power of each cryoprobe within a tumor is thus ascertained and adjusted by manual or automatic control, to account for heat sink differences at each cryoprobe location. A more controlled, symmetrical freeze that carefully covers all tumor margins is obtained. The cryoprobe power levels are set in proportion to each heat sink condition that the individual cryoprobes are experiencing at each of their locations.

Figure 4A:
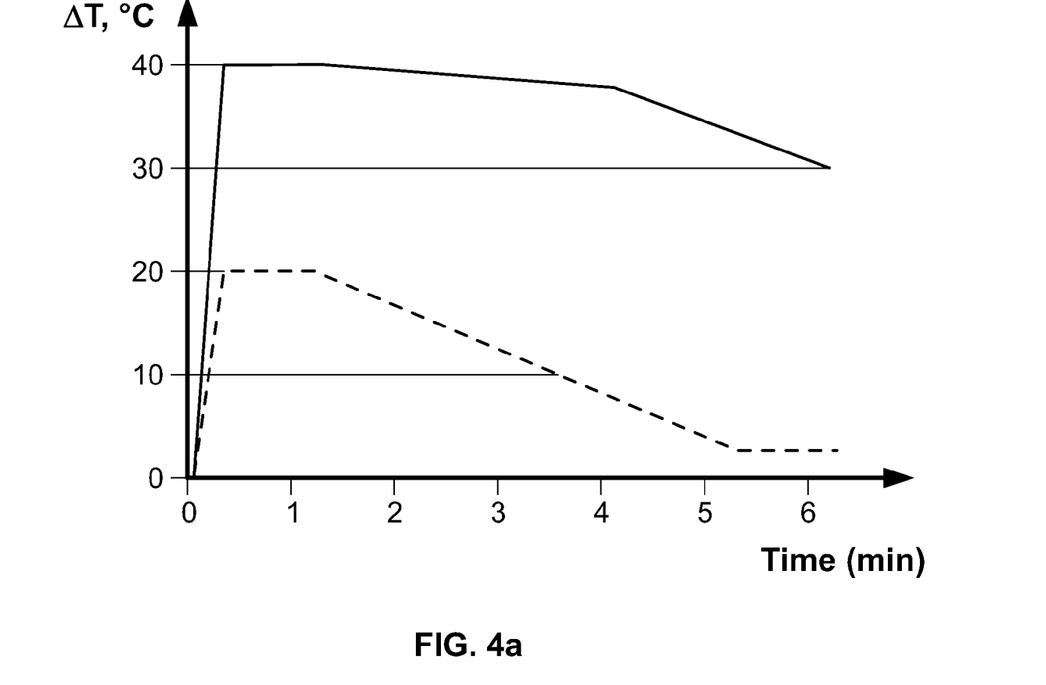
FIG. 4a is a graph showing a heatload difference provided by probe for peri-vascular (solid line) and non-vascular target tissue (dashed line).

FIG. 4a is a graph that shows the modeled or planned temperature difference $\Delta T$ between ingoing and outgoing cryogen as a diagnostic parameter of tissue freezing according to proximity of an adjacent vascularity. Peri-vascular probe location (solid line) may experience twice the initial heatload compared with non-vascular probe location, and may show very slow ice formation as depicted by very slow drop in $\Delta T$ until after 4 minutes of active freezing. Non-vascular probe location (dashed line) displays ice formation and growth as progressive drop in $\Delta T$ from 1 to 5 minutes, after which the ice stabilizes and steady state is reached.

Figure 4B:
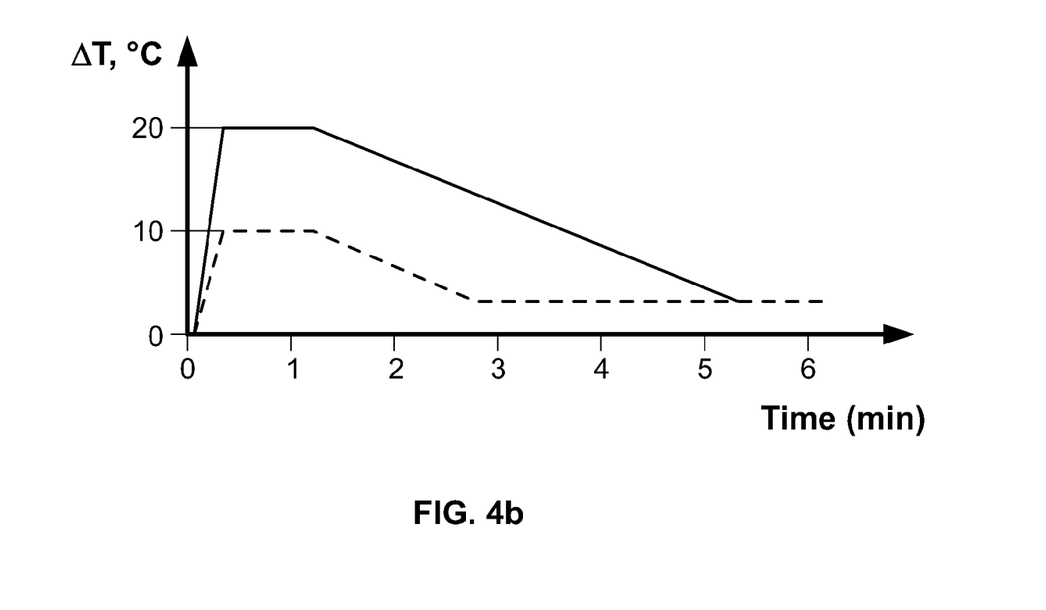
FIG. 4b is a graph showing heatload difference between two stages of freeze (first freeze=solid line; second=dashed line) of target tissue with high water content and without adjacent vascularity.

Well-perfused tissue with high water content and/or good thermal conductivity, (e.g., tumor of the kidney cortex), freezes thoroughly with excellent outcomes. This case is shown in FIG. 4b as two stages of freezing with different initial heatload $\Delta T=20°$ C. for the first freeze (solid line) and $\Delta T=10°$ C. for the second freeze (dashed line). Upon freezing, the renal tumors have an initial heat sink prior to ice formation due to the energy required to overcome the well-perfused cortical tissue, which is reflected by a modest $\Delta T$. The "watery" tumor and similar vascularity of the surrounding normal cortex would present a steadily decreasing heat sink over time as ice continues to grow. A steady state at a very low $\Delta T$ would develop when no further ice growth is noted. This represents a low progression of overcoming the microvasculature, turning it into a highly thermally conductive, water-based ice. Once ice is formed, the heatload is progressively lessened since it overcame the energy required for the phase-change, as well as ice now having four-fold the thermal conductivity of liquid water (i.e., 0.61 W/mK for water vs. 2.4 W/mK for ice). However, the growing ice will eventually hit static point where iceball size stabilizes and "$\Delta T$-time" curve flattens (e.g., 3° C. at the 5.5 minute mark for first freeze line in FIG. 4). During the thaw (not shown) between the two freezes, the heatload increases from the periphery as the ice slowly melts, but the bulk of the ice remains. Upon re-freezing with the second freeze, the probe experiences a lower initial heat load, and then $\Delta T$ decreases at a similar rate as ice grows until it reaches its steady state already at 3 minutes.

Figure 5:
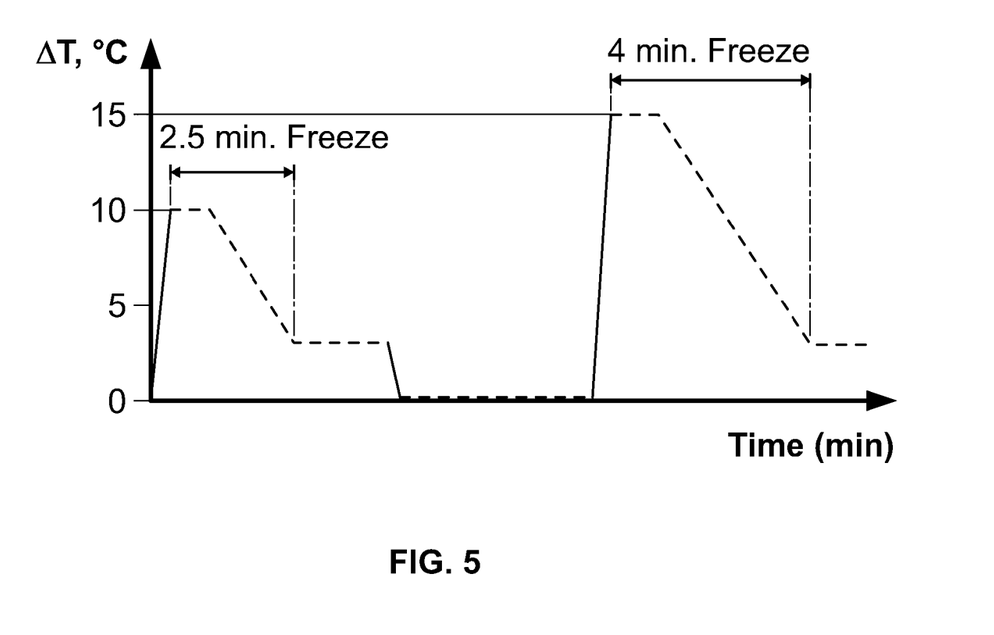
FIG. 5 is a graph showing a heatload difference for two stages of freeze of a fibrous target tissue without adjacent vascularity.

FIG. 5 shows a thermal response of a highly fibrous or low thermal conductivity tissue, such as peripheral lung parenchyma (i.e., without adjacent vasculature), that may have a lower initial heat load than kidney due to low thermal conductivity of the air-filled parenchyma surrounding the tumor acting as an insulator during the first freeze. In other words, the $\Delta T$ on the first freeze may only be 10° C., rather than the 20° C. noted for the second freeze on FIG. 4. However, during the thaw phase between two freezes, more edema or tissue oozing may create greater local thermal conductivity from the fluid. Therefore, during the initial few minutes of the second freeze, a greater initial heat sink may be experienced by the cryoprobe, such as 15° C. In addition, it takes longer time for the second freeze to reach steady-state (i.e., 4 min vs. 2.5 min) since a larger ice ball is now encompassing the more conductive "watery" tissues now surrounding the tumor.

Similarly, the fibrous background of cirrhosis during freezing of a primary liver tumor (i.e., hepatoma, hepatocellular carcinoma, or HCC) may start with higher initial heat load (e.g., $\Delta T$ ~20° C.) due to a hypervascular tumor (i.e., larger initial local volume of microvasculature). After the ice had progressed through the tumor volume, the $\Delta T$ may begin to flatten quicker, like in lung, due to the lower thermal conductivity of fibrous liver and relative insulating effect of cirrhotic liver. These hypothetical patterns suggest that each tumor and surrounding tissue may have characteristic changes that allow tissue to be frozen with rapid adjustments to changing local conditions during the freeze.

The above described volumetric ablation planning can now be used for comparison to actual or live procedural data and the probe positions and power settings may be corrected and adjusted for differences in eventual probe position within target tissue, local heat load findings, as well as faster treatment cycles with greater control of protection measures for adjacent structures. These adjustments or corrections during ablation procedure include but are not limited to: a) correcting the assumptions of the initial volumetric treatment plan; b) balancing initial probe power needs to achieve a symmetric freeze; c) adjusting freeze times of each probe at each needed power level; d) driving the necessary heating profiles of protective devices, described below; e) alter treatment during thaw phase (after first freeze) for more thorough second freeze coverage.

Currently, volumetric treatment plans can be corrected by noting the differences in planned vs. eventual probe placement using current 3D volume acquisitions by CT (or MRI), during or after the first freeze cycle. However, this requires estimated local tissue conditions for vascular heatload since no feedback currently exists. But with the present invention using high thermal conductivity probes and cryogens, tissue feedback during even the initial "stick freeze" phase (i.e., short non-ablative cold cycle for fixing probes in tissue within minimal ice formation) is used to characterize and anticipate the overall subsequent freeze response. In one embodiment, both peri-vascular and perfusion effects, as well as tissue consistency parameters of thermal conductivity and capacity of both the tumor and adjacent organ tissue are surmised before the first freeze is initiated. Therefore, the actual heat-load conditions of the probe, or $\Delta T$, within target tissue volume will validate any computer simulation of a treatment plan, thus allowing partial correction the treatment plan before initiating the first freeze cycle. However, even this correction cannot fully account for changes in tissue characteristics during the freeze.

Balancing probe power needs and adjusting their associated freeze times is done during the freeze by using the tissue feedback parameters of individual probe heatload signatures. All initial tissue assumptions will significantly change as ice is formed, which then occludes microvasculature and further changes thermal conductivity of local tissue. In one embodiment of the present invention, probe power requirements are automatically continually adjusted to maintain a "balanced" freeze, whereby all probes are all driven to obtain the overall objective of producing cytotoxic tissue temperatures throughout the tumor. The invention also includes adjusting power, location, number of probes, etc., manually.

Noting these changes in multiple probes over time would be much easier managed by an automated program. This program may only require the additional imaging measurements of the distances from the tumor margin to each probe (i.e., <1 cm from "1-2 rule") and the final interprobe spacing near midtumor. The heatload feedback from the cryoprobes would then drive each cryoprobe as long, and as strong, as necessary to push the lethal ice beyond all estimated tumor margins. Therefore, the entire freeze protocol may be more rapidly completed by optimizing probe functional capacities according to $\Delta T$ signatures of tissue response around each probe.

In addition to the steps described above, safety can be further improved by protecting adjacent crucial structures from thermal injury. Currently, this may be done "on the fly" by the physician injecting fluid such as saline, or placing balloons before an ice margin progresses near bowel, nerve or other crucial structure. However, the current techniques are somewhat undesirable in that they rely heavily on the manual and "on the fly" skill of the physician. In contrast, the present invention improves the thermal ablation procedure by providing various inputs and automatic safeguards. In particular, in one embodiment of the present invention, a protection device is linked to the monitoring system and is used as an additional input parameter to the treatment planning system as an automated safety feature. As an example, a thermocouple on an injection needle could provide a thermal input which would then only trigger an intermittent and/or continuous injection of warmed saline (e.g., 37-42° C.) when a certain target temperature was reached (e.g., <10° C.). This injection would provide appropriate distension of the space between the iceball and the crucial structure, raising the temperature at the thermocouple. This feedback loop would then shut off the injection.

The needle itself could also be envisioned as both a sensing and heating element to provide a protective barrier against ice progression if multiple such sensor/probe-"heaters" are used. These probes could be direct heating (e.g., electrical) or use internal circulating heated fluid in a multi-functional manner, such that the fluid could be switched to cryogen as needed.

A unique diagnostic aspect of the present invention is that the protection needle could also use heat difference to help characterize the tissues outside the ablation zone (e.g., a diagnostic means). Namely, the heat difference between even short bursts of a warm fluid now circulating within the needle-sensor-probe could be done to avoid surrounding tissue damage from the heat itself. This could also be done with circulating cryogen as needed for a short diagnostic pulse of the cryogen that also helps "stick" the needle-sensor-probe in place. This multi-functional probe could also be switched to a therapeutic setting (e.g., colder cryogen at greater power and duration) if greater freeze capacity is needed at the peripheral location. Similarly, the heat setting of the device could provide a therapeutic aspect by increasing local heating around the probe to >60° C. for ~<1 min to provide coagulation. This could also be conceived for every cryoprobe, not only for the thaw function to release the cryoprobe after the ablation is completed, but also to coagulate the puncture track as the probe is withdrawn.

Another embodiment of the invention includes using $\Delta T$ signatures of tissue response for automated freeze control to assist with the decision to place an additional probe, or re-adjust the current placement and configuration of existing probes. This embodiment includes the step of analyzing the $\Delta T$ signatures during, or after a freeze application. For example, $\Delta T$ signatures of one or more probes are analyzed for: (1) a disproportionately high initial $\Delta T$ that persisted, (2) slower ice formation, or shallower slope of $\Delta T$ than expected (or planned according to the planning signature), and/or (3) lack of achieving a steady-state at low $\Delta T$. Following analysis and or comparison of the $\Delta T$ signatures, the present embodiment includes, but is not limited to re-adjustment of probe location during thaw phase, and/or adding another probe to help overcome heatload and achieve complete ablation for that tumor region. Additionally, the method could be repeated for additional freeze applications until ultimately, a final freeze status matches or converges with the expected or planned $\Delta T$ signature and provides the physician and patient with confidence that thorough ablation had been performed of the target tumor. An optimization technique may be employed using a software program to minimize a value of a function, namely, to minimize the difference between the signatures.

All publications, patent and patent applications referenced herein are incorporated by reference in their entirety.

We claim:

1. A system for use with at least one cryoprobe for the treatment of biological tissue with thermal ablation, the system comprising:
    at least one cryoprobe comprising a distal treatment portion, an exchange chamber in said distal treatment portion, an inflow conduit transporting a cryogen towards said exchange chamber of the distal tissue treatment portion, and an outflow conduit for transporting said cryogen from said exchange chamber of the distal tissue treatment portion;
    an inflow temperature sensor at a first location along the inflow conduit and configured to detect an inflow temperature of the cryogen flowing through said inflow conduit at the first location;
    an outflow temperature sensor at a second location along the outflow conduit and configured to detect an outflow temperature of the cryogen flowing through said outflow conduit at the second location; and
    a processor programmed to
        receive procedure data comprising a cryogen flowrate, the inflow temperature and the outflow temperature over time;
        calculate a procedure signature based on the cryogen flowrate and a temperature difference between said inflow temperature and said outflow temperature over time;
        compare the procedure signature to a planning signature, said planning signature based on previously acquired image data of said tissue; and
        adjust power to the at least one cryoprobe based on comparing said procedure signature to said planning signature.

2. The system of claim 1 wherein said planning signature is a planning isotherm volume of tissue and said procedure signature is a tissue volume isotherm obtained during or immediately after the procedure.

3. The system of claim 1 wherein said processor is further programmed to automatically regulate the cryogen flowrate of said cryogen to said at least one cryoprobe.

4. The system of claim 1 wherein said processor is further programmed to automatically regulate the temperature of said cryogen to said at least one cryoprobe.

5. The system of claim 1 wherein said processor is further programmed to determine said planning signature.

6. The system of claim 5 wherein said processor is further programmed to receive manual input.

7. The system of claim 5 wherein said processor is programmed to compute said planning signature based on previously acquired image data of a marker deposited in said tissue.

8. The system of claim 5 wherein said processor is programmed to compute said planning signature based on a presence of a blood vessel in proximity to the tissue.

9. The system of claim 1 wherein said processor is further programmed to calculate the procedure signature based on procedure data comprising live image data.

10. The system of claim 1 further comprising a refrigerator for cooling said cryogen.

11. The system of claim 10 further comprising a cryogen tank, said cryogen tank in fluid communication with said cryoprobe.

12. The system of claim 11 further comprising a pump to drive the cryogen from the cryogen tank and along the inflow conduit and outflow conduit.

13. The system of claim 1 wherein the first location and the second location are within the distal treatment portion of the cryoprobe.

14. The system of claim 13 wherein the cryogen has a freezing point less than −90 degrees C.

15. The system of claim 14 wherein said cryogen is one liquid selected from the group of propane, perfluropropane, Refrigerant 124, and Refrigerant 1270.

16. The system of claim 1 wherein said processor is further programmed to stop treatment if the procedure signature matches the planning signature.

17. The system of claim 1 wherein said processor is further programmed to adjust the cryogen flowrate to force the procedure signature to converge with the planning signature.

18. The system of claim 1 wherein said at least one cryoprobe includes a plurality of cryoprobes.

* * * * *